United States Patent [19]

Keith et al.

[11] 4,393,003
[45] Jul. 12, 1983

[54] β-LACTAMASE INHIBITORS

[75] Inventors: Dennis D. Keith, Montclair; John P. Tengi, Cedar Grove; Manfred Weigele, North Caldwell, all of N.J.

[73] Assignee: Hoffmann-La Roche Inc., Nutley, N.J.

[21] Appl. No.: 252,106

[22] Filed: Apr. 8, 1981

[51] Int. Cl.³ ................. C07D 499/00; A61K 31/425
[52] U.S. Cl. .............................. 260/245.2 R; 424/270; 260/245.4
[58] Field of Search ...................... 260/245.2; 424/270

[56] References Cited
U.S. PATENT DOCUMENTS 4,282,150  8/1981  Menard et al. ...................... 424/270

Primary Examiner—Nicholas S. Rizzo
Attorney, Agent, or Firm—Jon S. Saxe; Bernard S. Leon; Frank P. Hoffman

[57] ABSTRACT

A β-lactamase inhibitor of the formula

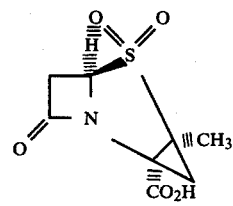

I and the pharmaceutically acceptable salts thereof are presented.

Also presented are intermediates and synthetic processes for the manufacture of the formula I compound.

The compound inhibits the activity of enzymes which inactivate certain βlactam antibiotics.

6 Claims, No Drawings

β-LACTAMASE INHIBITORS

DESCRIPTION OF THE INVENTION

The present invention relates to a novel β-lactamase inhibitor of the formula

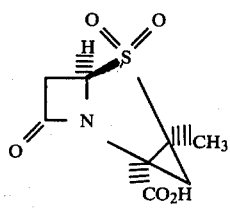

I and the pharmaceutically acceptable salts thereof.

The pharmaceutically acceptable salts of the compounds of formula I are prepared from the free acid by methods well-known in the art, for example, by treating the free acid in solution with a suitable base or salt. Examples of basic substances capable of forming such pharmaceutically acceptable salts for the purpose of the present invention include alkali metal bases, such as, sodium hydroxide, potassium hydroxide, lithium hydroxide and the like; alkaline earth metal bases, such as, calcium or magnesium hydroxide and the like and ammonium hydroxide. Alkali metal or alkaline earth metal salts suitable for forming pharmaceutically acceptable salts can include anions, such as, carbonate and bicarbonate. Preferred for use in this invention are salts formed from alkali metal bases.

The following schemes set forth various steps to synthesize the compound of formula I.

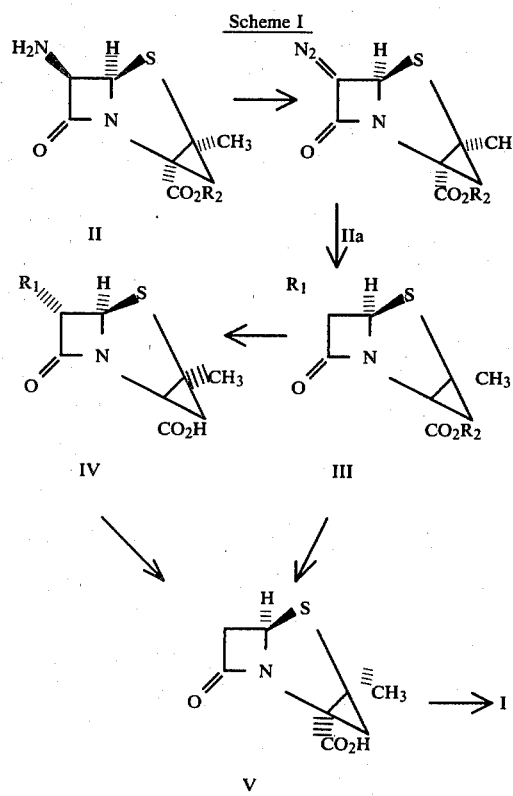

wherein $R_1$ is chloro, bromo or iodo and $R_2$ is H or a conventional carboxy protecting group.

The identity of the carboxy protecting group is not critical, as long as conditions for its subsequent removal are compatible with the β-lactam ring system. Among the preferred carboxy protecting groups are, for example, $C_1$ to $C_7$ alkyl groups, unsubstituted and substituted benzyl groups, e.g., nitrobenzyl or a benzhydryl group and the 2,2,2-trichloroethyl group.

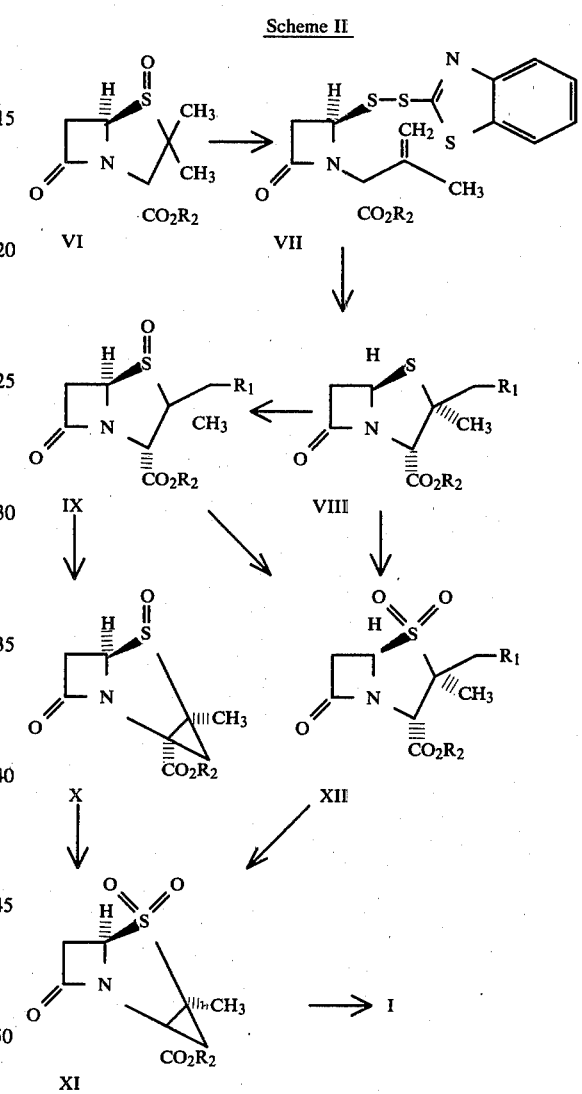

wherein $R_1$ and $R_2$ are as above.

II→III

The compounds of formula II are known, having been disclosed in U.S. Pat. No. 3,904,607 to Kamiya et al. (1975).

The compound of formula II is reacted in aqueous solution with a nitrosating agent, such as, an alkali metal nitrite, e.g., sodium nitrite in conjunction with an inorganic acid, e.g., sulfuric acid followed by reaction with a source of halide ions, such as, an alkali metal halide, e.g., sodium chloride, bromide or iodide. Alternatively, hydrochloric, hydrobromic or hydroiodic acid can be used directly with sodium nitrite. This part of the reaction is run at between −10° to 5° C. with about −5° C. to 0° C. as preferred.

Thereafter, for the purpose of facilitating purification by chromatographic means, the compound of formula III (if $R_2=H$) is esterified by standard means, preferably utilizing diazomethane or an alkyl, dialkyl, aryl or diaryl diazomethane, which are well-known in the art. This esterification reaction is carried out in an inert solvent, preferably in a halogenated hydrocarbon, such as, methylene chloride or in an ether, such as, diethyl ether or dioxane. The reaction is run at 0° C. to 40° C., with room temperature preferred. Alternately the compound of formula III (where $R_2=H$) is converted to the 2,2,2-trichloroethyl ester utilizing trichloroethyl chloroformate in the presence of pyridine as a base with an inert co-solvent. Acetone is an example of an inert co-solvent. This esterification is carried out at −5° C. to 35° C., with room temperature being preferred.

III→IV

After purification by standard chromatographic means, the compound of formula III (where $R_2$ is a carboxy protecting group as defined above) is subjected to ester cleaving conditions, which will be dictated by the nature of the carboxy protecting group. For example, standard base or acid mediated hydrolysis is preferred when $R_2$ is a simple alkyl. When $R_2$ is a diarylmethyl group, e.g., benzhydryl, removal of the ester group is achieved by reaction with a strong acid in a polar, anhydrous solvent. A preferred strong acid, which also serves as solvent is trifluoroacetic acid. An alternative strong acid is e.g., hydrogen chloride, when used in a polar solvent (e.g., nitromethane or sulfolane). It is advantageous to carry out the removal of the diarylmethyl ester group in the presence of a cation scavenger, e.g., anisole. The reaction temperature in these processes may vary between about −15° C. to room temperature, with about 0° C. preferred.

IV→V

The compound of formula IV is reductively dehalogenated by catalytic hydrogenation or by dissolving metal reduction. If dehalogenation is achieved by catalytic hydrogenation, a transition metal catalyst, such as palladium on carbon, is used. Pressure of hydrogen can vary between atmospheric pressure and approximately 100 psi. Solvents used in this hydrogenation can include water, lower alkanols, ethyl acetate or other polar solvents, such as, acetonitrile. It may be advantageous to carry out the hydrogenation in a mixture of the above solvents. The hydrogenation is carried out in the presence of an acid scavenger, such as, alkali metal bicarbonate, e.g., $NaHCO_3$ or an alkaline earth metal carbonate. The reaction temperature may vary from about 0° C. to 50° C. with about room temperature as preferred. If dehalogenation is achieved by dissolving metal reduction, a preferred mode utilizes reaction with zinc in acetic acid. The temperature used for this reaction may vary from 0° C. to 50° C., with room temperature preferred.

III→V

Alternatively, if $R_2$ in formula III is benzyl, substituted benzyl, dialkylmethyl or trichloroethyl, the conversion of formula III to formula V may be accomplished directly, i.e., removal of the carboxy protecting group $R_2$ and the halogen $R_1$ are achieved in a single reduction step. Thus, if $R_2$ is benzyl, substituted benzyl or dialkylmethyl, the catalytic hydrogenation, specified above, (IV→V), will effect direct conversion of formula III to formula V. If $R_2$ is trichloroethyl, reaction of formula III with zinc in acetic acid as above will directly afford formula V. The reaction conditions are as set forth in step IV→V. It should be noted that a non-isolated intermediate compound wherein $R_1$ is removed but $R_2$ remains may be formed but will eventually be converted to the compound of formula V under continuing reductive conditions.

V→I

The compound of formula V is converted to the compound of formula I by oxidation with potassium permanganate. The reaction is carried out in aqueous acetic acid at a temperature between −5° C. and 30° C., with about 0° C. preferred. Alternately, the oxidation of the compound of formula V to the compound of formula I can be achieved with peroxy acids, such as, for example, m-chloroperbenzoic acid, peracetic acid, pertrifluoroacetic acid, 2,4-dinitroperbenzoic acid. The reaction of V with peroxy acids is conveniently carried out in an inert organic solvent, such as the chlorinated hydrocarbons, e.g., chloroform, methylene chloride, at a temperature of −10° C. to 50° C. with room temperature preferred.

VI→VII

The compound of formula VI is a known compound, the esters of which are disclosed in U.K. patent application No. 2000138A along with the methods to produce the compounds. For the conversion to a compound of formula VII the compound of formula VI is reacted with a heteroaromatic thiol, such as, 2-mercaptobenzothiazole. Suitable reaction solvents include aromatic hydrocarbons, such as, toluene, xylene or benzene. The reaction temperature may be varied from about 50° C. to 150° C. with reflux temperature of the selected solvent as preferred.

VII→VIII

The compound of formula VII is thereafter converted to a compound of formula VIII by reaction with bromine, chlorine or iodine in an inert solvent, such as the halogenated hydrocarbon, e.g., methylene chloride or chloroform in the presence of an acid scavenger, e.g., calcium oxide or polymeric vinyl pyridine or propylene oxide. The reaction temperature may be varied between about −20° C. to room temperature with about −10° C. as preferred.

VIII→IX; VIII→XII; IX→XII

The compound of formula VIII is thereafter oxidized to a compound of formula IX utilizing peracids, such as, m-chloroperbenzoic acid, peracetic acid, pertrifluoroacetic acid, or 2,4-dinitroperbenzoic acid. Suitable reaction solvents for this reaction include aromatic hydrocarbons, e.g., benzene or toluene or a halogenated hydrocarbon, such as, methylene chloride or chloroform. The reaction temprature may be varied from about −10° C. to 50° C. with about 0° C. preferred. Alternatively, the oxidation of formula VIII to a compound of formula IX can be accomplished with sodium periodate or potassium periodate. In this case the reaction is carried out in a mixed solvent consisting of water and a lower alcohol, e.g., methanol or ethanol, at a temperature of 0° C. to 50° C., with room temperature preferred.

If an excess of the oxidant is employed, the compound of formula VIII is converted via a compound of formula IX to a compound of formula XII.

IX→X; XII→XI

The compounds of formulas IX or XII are converted to compounds of formula X or XI by reaction with a base, such as, an organic amine base, e.g., a tertiary amine base, such as, 1,4-diazabicyclo[2.2.2]octane or 1,5-diazabicyclo[5.4.0[nonane in a polar organic solvent, such as, dimethylformamide, dioxane or tetrahydrofuran. The reaction temperature may be varied from about −50° C. to 0° C. with about −30° C. as preferred.

X→XI

The compound of formula X is oxidized to a compound of formula XI utilizing peroxy acids such as m-chloroperbenzoic acid, peracetic acid, pertrifluoroacetic acid, 2,4-dinitroperbenzoic acid. The reaction of formula X with peroxy acids is conveniently carried out in an inert organic solvent such as the chlorinated hydrocarbons, e.g., chloroform, methylene chloride at a temperature of −10° C. to 50° C., with room temperature preferred.

XI→I

Conditions described for the conversion of a compound of formula III to a compound of formula IV and formula III to formula V are utilized for the analogous conversions of compounds of formula XI to compounds of formula I.

The utility of the compound of formula I is indicated by the β-lactamase inhibition activity as observed in the cell-free enzyme assay below.

Cell-Free Enzyme Assay

The test compound is preincubated with enzyme for 20 min. at 30° C. and pH 7. Chromogenic cephalosporin substrate, nitrocefin, is added and its initial rate of hydrolysis is recorded spectrophotometrically. Three enzyme preparations were employed:

(a) the inducible penicillinase from *Staphylococcus aureus* 1059B, (b) the constitutive broad-spectrum TEM type beta-lactamase mediated by the resistance transfer factor R1 in *Escherichia coli* 1263B, and (c) the type Ia cephalosporinase from *Enterobacter cloacae* purchased from Miles Laboratories.

Included for comparison purposes were the antibiotics cloxacillin and dicloxacillin. $I_{50}(\mu M)$ is calculated as the concentration necessary to inhibit the rate of nitrocefin hydrolysis by 50%.

|  | $I_{50}$ ($\mu M$) | | |
|---|---|---|---|
|  | Staphylococcus aureus | Escherichia coli R1 | Enterobacter cloacae |
| Dicloxacillin | 96 | 32 | 0.0014 |
| Cloxacillin | 365 | 68 | 0.0015 |
| 2S-(2α,4α,6α)-4-Methyl-8-oxo-5-thial-1-azatricyclo-/4.2.0.0/2/4/octane-2-carboxylic acid 5,5-dioxide (the compound of formula I) | 6.7 | 1.1 | 69 |

The compound of formula I also exhibits utility as a compound to potentiate the activity of penicillins and cephalosporins which are known in the art. This activity is illustrated by the test and results below:

The efficacy of putative β-lactamase inhibitors is assessed by determining the effect of the test compounds on the minimal inhibitory concentrations (MICs) of β-lactamase-sensitive antibiotics against bacterial strains known to produce β-lactamases.

The antibacterial activity of the β-lactamase inhibitor against the test strains is determined by a standard agar dilution method. Serial two-fold dilutions of the β-lactamase inhibitor are prepared in water to give concentrations 10 times the final desired concentrations. The aqueous dilutions are then further diluted 1:10 in Mueller-Hinton (MH) agar. These agar mixtures are poured into petri plates and allowed to harden. Each plate, including a drug-free control plate, is inoculated by means of a Steers replicator with 0.05 mL of $10^{-4}$ dilutions of the test organisms. The $10^{-4}$ dilutions of the organisms are prepared in MH broth from overnight TS broth cultures. The plates are examined for growth after overnight incubation at 37° C. The lowest drug concentration at which three or fewer colonies are observed is considered to be the MIC.

The β-lactamase inhibitor is then tested for potentiation of the antibiotic mecillinam. Aqueous solutions are prepared containing serial two-fold dilutions of mecillinam in the presence of the β-lactamase inhibitor at a constant concentration 2–4 fold less than its MIC for the most sensitive of the test organisms. The same procedure as above is then followed. Controls include a drug-free plate and a plate containing the β-lactamase inhibitor at the concentration used in the test. The MIC of mecillinam as a single agent is also determined at the same time.

| In Vitro Evaluation of β-Lactamase Inhibitors (MIC:μg/mL)[1] | | | |
|---|---|---|---|
|  | Compound of Formula I | Mecillinam | Compound of Mecillianam plus Formula I (8 μg/mL) |
| E. Cloacae P99 | Inert | 0.03 | <0.008 |
| E. Coli 7289 | Inert | 32 | 0.5 |
| E. Coli K12R1 | Inert | 1 | 0.06 |
| E. Coli ST 323 | Inert | 4 | 0.06 |
| S. Marcescens S5 | Inert | 4 | 2 |
| P. Aeruginosa 5700 | Inert | >128 | >128 |

As used throughout the specification the penicillin carboxy protecting group denominated as $R_2$ can be any carboxy protecting group conventionally used in the penicillin art to protect carboxy groups at the 3-position. The protecting group must be stable during reaction steps, such as, oxidations which the intermediate compounds undergo but must be removable from the immediate precursor of the compund of formula I using conditions under which the β-lactam ring remains substantially intact.

As utilized in the present specification, the term "lower alkyl" or "alkyl" refers to both straight and branched chain $C_1$ to $C_7$ carbon-hydrogen radicals, preferably $C_1$ to $C_4$ carbon-hydrogen radicals, such as, methyl, ethyl, propyl, isopropyl, butyl and the like.

As utilized herein the terms, "halogen" or "halo" stand for the chlorine, bromine or iodine members of the class.

As utilized in the present specification the term "aryl" refers to an organic radical derived from a substituted or unsubstituted hydrocarbon by the removal of one atom, e.g., benzyl, nitrobenzyl or chlorobenzyl.

The following examples are illustrative, but not limitative of this invention. All temperatures given are in degrees centigrade, unless indicated otherwise.

EXAMPLE 1

[2S-(2α,4α,6α,7α)]-7-Bromo-4-methyl-8-oxo-5-thia-1-azatricyclo[4.2.0.0²,⁴]octane-2-carboxylic acid diphenylmethyl ester A solution consisting of 1.74 g (8.1 mmol) of [2S-(2α,4α,6α,7β)]-7-amino-4-methyl-8-oxo-5-thia-1-azatricyclo[4.2.0.0²,⁴]octane-2-carboxylic acid ¹, 4.56 g (44.3 mmol) of sodium bromide and 22 mL of 2 N sulfuric acid was cooled to −5°. To this was added dropwise 0.954 g (13.8 mmol) of sodium nitrite in 5 mL of water. The reaction was stirred at 0° for 30 min, allowed to warm to 15°, and extracted with two 30 mL portions of methylene chloride. The combined methylene chloride extracts were dried over anhydrous sodium sulfate, filtered, and the filtrate treated with a slight excess of freshly prepared diphenyl diazomethane in methylene chloride. After stirring for 15 minutes, the reaction was concentrated on the rotary evaporator to yield an amber foam.

[1] T. Kamiay, et al., Ger. Offen. No. 2,358,178 (1974), cf. *Chem. Abstr.* 81, 49672 j(1974).

The foam was chromatographed on silica gel 60 (70–230 mesh) using ethyl acetate (1)/cyclohexane(9) to elute. The appropriate fractions were combined and concentrated to yield [2S-(2α,4α,6α,7α)]-7-bromo-4-methyl-8-oxo-5-thia-1-azatricyclo[4.2.0.0$^{2,4}$]octane-2-carboxylic acid diphenylmethyl ester as a yellow foam.

EXAMPLE 2

[2S-(2α,4α,6α,7α)]-7-Bromo-4-methyl-8-oxo-5-thia-1-azatricyclo-[4.2.0.0$^{2,4}$]octane-2-carboxylic acid A solution consisting of 0.86 g (1.94 mmol) of [2S-(2α,4α,6α,7α)]-7-bromo-4-methyl-8-oxo-5-thia-1-azatricyclo[4.2.0.0$^{2,4}$]octane-2-carboxylic acid diphenylmethyl ester and 4.2 mL of anisole was cooled to 0° and 22 mL of trifluoroacetic acid was added at once. The resultant solution was stirred at 0° for 1 hr. The then dark amber solution was concentrated in vacuo and the residue chromatographed on silica gel 60 (70–230 mesh). The column was eluted with ethyl acetate (25)/EAW-632 is a solution consisting of ethyl acetate (6)/acetic acid (3)/water (2). The appropriate fractions were combined and concentrated in vacuo to yield [2S-(2α,4α,6α,7α)]-7-bromo-4-methyl-8-oxo-5-thia-1-azatricyclo[4.2.0.0$^{2,4}$]octane-2-carboxylic acid as a light amber oil.

EXAMPLE 3

[2S-(2α,4α,6α,7α)]-4-Methyl-8-oxo-5-thia-1-azatricyclo[4.2.0.0$^{2,4}$]-octane-2-carboxylic acid A mixture consisting of 0.494 g (1.78 mmol) of [2S-(2α,4α,6α,7α)]-7-bromo-4-methyl-8-oxo-5-thia-1-azatricyclo[4.2.0.0$^{2,4}$]-octane-2-carboxylic acid, 0.75 g (8.9 mmol) of sodium bicarbonate, 0.5 g of 10% Pd/charcoal and 50 mL of water was stirred under hydrogen at ambient temperature and atmospheric pressure for 2 hrs. The mixture was filtered and the pH of the filtrate adjusted to 2.0 with 2 N hydrochloric acid. The aqueous solution was extracted two times with 60 mL of ethyl acetate. The extracts were combined, washed with brine, dried over anhydrous sodium sulfate, and concentrated in vacuo to yield a white solid. Recrystallization from methanol/ether/petroleum ether gave pure [2S-(2α,4α,6α,7α)]-4-methyl-8-oxo-5-thia-1-azatricyclo[4.2.0.0$^{2,4}$]octane-2-carboxylic acid mp 153°–157°.

EXAMPLE 4

[2S-(2α,4α,6α)]-4-Methyl-8-oxo-5-thia-1-azatricyclo[4.2.0.0$^{2,4}$]octane-2-carboxylic acid 5,5-dioxide A solution consisting of 0.158 g (1 mmol) of acetic acid, and 3 mL of water was cooled to 0°. To the cooled, stirred mixture was added dropwise at a rate to maintain the temperature between 0° and 5° a solution consisting of 0.1 g (0.5 mmol) of [2S-(2α,4α,6α)]-4-methyl-8-oxo-5-thiatricyclo[4.2.0.0$^{2,4}$]octane-2-carboxylic acid, 0.042 g (0.5 mmol) of sodium bicarbonate and 2 mL of water. The reaction mixture was stirred at 5° for 20 minutes after addition was complete. Excess permanganate was destroyed by the addition of sodium bisulfite. The mixture was then filtered through Celite, and the pH of the filtrate was adjusted to 2 with 2 N hydrochloric acid. The aqueous solution was extracted two times with 25 mL portions of ethyl acetate. The combined extracts were washed with brine, dried over anhydrous sodium sulfate and concentrated in vacuo to yield a white solid. Recrystallization from methanol/ether/petroleum ether gave [2S-(2α,4α,6α)]-4-methyl-8-oxo-5-thia-1-azatricyclo[4.2.0.0$^{2,4}$]octane-2-carboxylic acid 5,5-dioxide: mp 177°–179°.

EXAMPLE 5

[2S-(2α,5α,6α)]-6-Bromo-3,3-dimethyl-7-oxo-4-thia-1-azabicyclo[3.2.0]heptane-2-carboxylic acid A round-bottom flask equipped with magnetic stirrer and internal thermometer was charged with 34.56 g (0.153 mol) of 6-β-aminopenicillanic acid, 400 mL of 2.5 N sulfuric acid, and 83.2 g (0.808 mol) of sodium bromide. To the stirred, cooled (internal temperature 0°) solution was added dropwise over a period of approximately 15 minutes a solution consisting of 17.0 g (0.246 mol) of sodium nitrite and 80 mL of water (internal temperature less than 5° C.). Nitrogen evolution caused considerable foaming which was controlled by the addition of 25 mL of ether. The reaction was stirred at 0° for 1 h, allowed to warm to 15° and extracted with two 250 mL portions of ether and two 250 mL portions of chloroform. The organic extracts were combined and dried over anhydrous sodium sulfate. The solution was filtered and the filtrate treated with activated charcoal. The resulting mixture was filtered through Celite, and the filtrate concentrated on a rotary evaporator. The residue was dried in vacuo to yield [2S-(2α,5α,6α)]-bromo-3,3-dimethyl-7-oxo-4-thia-1-azabicyclo[3.2.0]heptane-2-carboxylic acid as a light yellow foam.

EXAMPLE 6

[2S-(2α,5α0]-3,3-Dimethyl-7-oxo-4-thia-1-azabicyclo[3.2.0]-heptane-2-carboxylic acid diphenylmethyl ester Two 500 mL Parr bottles were each charged with 10 g (35.7 mmol) of [2S-(2α,5α,6α)]-6-bromo-3,3-dimethyl-7-oxo-4-thia-1-azabicyclo[3.2.0]heptane-2-carboxylic acid, 200 mL of water, 12.0 g (0.142 mol) of sodium bicarbonate, and 2.5 g of 10% Pd/C. The mixture was hydrogenated on the Parr shaker at 20 lbs. pressure for 1½ hrs. The catalyst was removed by filtration and the filtrates from each Parr shaker were combined. The pH was adjusted to 2.0 with conc. HCl and the aqueous phase was extracted with two 250 mL portions of methylene chloride. Each extract was washed with the same 500 mL of brine. The combined methylene chloride extracts were dried over anhydrous sodium sulfate, and the mixture filtered.

To the filtrate was added a freshly prepared solution of diphenyl diazomethane in methylene chloride until the rose color of the diazo compound persisted. The solution was stirred for 15 minutes and 1 mL of glacial acetic acid was added to discharge the remaining diphenyl diazomethane. The resulting solution was concentrated on a rotary evaporator followed by drying under high vacuum to yield crude diphenylmethyl penicillinate as a yellow gum. This material could be used directly in the next example, or alternatively it could be purified by chromatography on silica gel 60 (70-230 mesh) using ethyl acetate (1)/cyclohexane (4) as eluent. Combining the appropriate fractions, followed by concentration in vacuo yielded [2S-(2α,5α)]-3,3-dimethyl-7-oxo-4-thia-1-azabicyclo[3.2.0]heptane-2-carboxylic acid diphenylmethyl ester.

EXAMPLE 7

[2S-(2α,5α)]-3,3-Dimethyl-7-oxo-4-thia-1-azabicyclo[3.2.0]heptane-2-carboxylic acid diphenylmethyl ester 4-oxide Method A.

A round-bottom flask was charged with 22.4 g (0.061 mol) of [2S-(2α,5α)]-3,3-dimethyl-7-oxo-4-thia-1-azabicyclo[3.2.0]heptane-2-carboxylic acid diphenylmethyl ester, and 200 mL of methanol. To the resultant solution was added dropwise over a period of 10-15 minutes, a solution consisting of 180 mL of 0.5 M sodium metaperiodate and 100 mL of methanol. The reaction mixture was stirred at room temperature for 15 hrs. During this time, a white precipitate was deposited.

The methanol was removed on a rotary evaporator (Temp <35°) and the remaining mixture was partitioned between 1 L of brine and 1 L of ethyl acetate. The layers were separated and the aqueous layer was extracted again with 1 L of ethyl acetate. The ethyl acetate extracts were washed with the same 1 L of brine, combined, and dried with anhydrous sodium sulfate. The mixture was filtered and the filtrate concentrated on a rotary evaporator until the sulfoxide began to crystallize. The solution was then removed from the rotary evaporator and warmed to dissolve the solids. Addition of ether/petroleum ether caused crystallization to begin. After cooling the mixture in the refrigerator, the solids were collected by filtration. Air drying yielded [2S-(2α,5α)]-3,3-dimethyl-7-oxo-4-thia-1-azabicyclo-[3.2.0]heptane-2-carboxylic acid diphenylmethyl ester 4-oxide: mp 158°-160° C.

Method B.

A solution consisting of 96.5 g (0.26 mol) [2S-(2α,5α)]-3,3-dimethyl-7-oxo-4-thia-1-azabicyclo[3.2.0]heptane-2-carboxylic acid diphenylmethyl ester and 1.2 L methylene chloride was cooled to −5° C. m-Chloroperbenzoic acid was added portionwise at a rate such that the reaction temperature was less than 0° C. The mixture was allowed to warm to 20° C. and was partitioned between ethyl acetate and water. The organic solutions were washed with brine, dried and concentrated to a volume of 600 mL. The resultant suspension was warmed to effect solution, treated with a small volume of petroleum ether to initiate crystallization, cooled and filtered to yield the title product. The NMR spectrum of this material was the same as the spectrum of the material isolated in Method A.

EXAMPLE 8

[R-(R*)]-2-[(2-Benzothiazolyl)dithio]-α-(1-methylethenyl)-4-oxo-1-azetidineacetic acid diphenylmethyl ester A round-bottom flask equipped with reflux condenser and Dean-Stark water separator was charged with 19.2 g (50 mmol) of [2S-(2α,5α)]-3,3-dimethyl-7-oxo-4-thia-1-azabicyclo[3.2.0]heptane-2-carboxylic acid diphenylmethyl ester 4-oxide, 8.55 g (51 mmol) of 2-mercaptobenzothiazole and 250 mL of toluene. The reaction mixture was heated at reflux temperature for 2 h. The solution was then cooled and concentrated in vacuo to yield [R-(R*)]-2-[2(-benzothiazolyl)dithio]-α-(1-azetidineacetic acid diphenylmethyl ester as an amber oil.

EXAMPLE 9

[2S-(2α,3β,5α)]-3-(Bromomethyl)-3-methyl-7-oxo-4-thia-1-azabicyclo-[3.2.0]heptane-carboxylic acid diphenylmethyl ester 4-oxide (both isomers)

A round-bottom flask was charged with 28.4 g (53.4 mmol) of [R-(R*)]-2-[(2-benzothiazolyl)dithio]-α-(1-methylethenyl)-4-oxo-1-azetidineacetic acid diphenylmethyl ester, 5.7 g (101.6 mmol) of calcium oxide and 350 mL of dry methylene chloride. The mixture was cooled to −10° with stirring and 125 mL of a solution consisting of 2.0 mL of bromine in 200 mL of methylene chloride was added dropwise. The reaction mixture turned light yellow and was stirred for 10 minutes at −10°. Cyclohexane (300 mL), ether (150 mL) and petroleum ether (150 mL) were added to the reaction and the stirring was continued at 0° for 5 minutes. The solids were removed from the reaction mixture by filtration through celite, and to the filtrate was added a solution consisting of 10.4 g m-chloroperbenzoic acid in 150 mL chloroform. The resulting solution was stirred at 0° C. for 30 min, washed with saturated sodium bicarbonate and with brine. The organic layer was dried over anhydrous sodium sulfate, filtered, and concentrated in vacuo to yield a yellow foam. The foam was chromatographed on silica gel (ethyl acetate/hexane; 2:3). The two possible sulfoxide isomers of [2S-(2α,3β,5α)]-3-(bromomethyl)-3-methyl-7-oxo-4-thia-1-azabicyclo[3.2.0]heptane-2-carboxylic acid diphenylmethyl ester 4-oxide were obtained. The sulfoxide eluted first, isomer A, was obtained as a white crystalline solid: mp 129°-132° C. dec. The sulfoxide isomer eluted second was obtained as a yellow foam.

EXAMPLE 10

[2S-(2α,4α,6α)]-4-Methyl-8-oxo-5-thia-1-azatricyclo[4.2.0.0$^{2,4}$]octane-2-carboxylic acid diphenylmethyl ester 5-oxide A round-bottom flask equipped with an argon bubbler was charged with 5.3 g (11.5 mmol) of [2S-(2α,3β,5α)]-3-(bromomethyl)-3-methyl-7-oxo-4-thia-1-azatricyclo[3.2.0]heptane-2-carboxylic acid diphenylmethyl ester 4-oxide, and 15 mL of dry N,N-dimethylformamide. The solution was cooled to −30° and a solution consisting of 1.82 g (11.9 mmol) of 1,5-diazabicyclo[5.4.0]undec-5-ene(DBU) and 15 mL of dry N,N-dimethylformamide was added dropwise. After addition was complete, the reaction mixture was stirred at −30° for 3 h, and poured into 250 mL of ethyl acetate. The resultant mixture was filtered through a cotton plug. The filtrate was washed two times with 0.2 N hydrochloric acid, two times with saturated sodium bicarbonate, and two times with brine/water (1:1). Each aqueous phase was backwashed with the same portion of ethyl acetate. The ethyl acetate solutions were combined, dried over anhydrous sodium sulfate, treated with activated charcoal, filtered and the filtrate concentrated in vacuo to yield a solid residue. The solid was triturated with ethyl acetate (1)/cyclohexane (1) to yield [2S-(2α,4α,6α)]-4-methyl-8-oxo-5-thia-1-azatricyclo[4.2.0.0$^{2,4}$]octane-2-carboxylic acid diphenylmethyl ester 5-oxide: mp 195°–7° dec.

EXAMPLE 11

[2S-(2α,4α,6α)]-4-Methyl-8-oxo-5-thia-1-azatricyclo[4.2.0.0$^{2,4}$]octane-2-carboxylic acid diphenylmethyl ester 5,5-dioxide Method A.

A round-bottom flask was charged with 1.64 g (4.3 mmol) of [2S-(2α,4α,6α)]-4-methyl-8-oxo-5-thia-1-azatricyclo[4.2.0.0$^{2,4}$]octane-2-carboxylic acid diphenylmethyl ester 5-oxide and 40 mL of chloroform. The resultant solution was cooled to 0° with stirring and a solution consisting of 1.02 g of m-chloroperbenzoic acid (80–90% pure) in 25 mL of chloroform was added dropwise. The reaction mixture was allowed to warm to and stir at room temperature. After 5 h, it was washed once with saturated aqueous sodium bicarbonate and once with brine. The organic phase was separated, dried over anhydrous sodium sulfate, filtered, and the filtrate concentrated in vacuo. Crystallization of the residue from ethyl acetate/ether/petroleum ether gave [2S-(2α,4α,6α)]-4-methyl-8-oxo-5-thia-1-azetricyclo[4.2.0.0$^{2,4}$]octane-2-carboxylic acid diphenylmethyl ester 5,5-dioxide as a white solid: mp 203°–6° dec.

Method B.

A flask was charged with 0.478 g (1 mmol) of [2S-(2,α,3β,5α)]-3-bromomethyl-3-methyl-7-oxo-4-thia-1-azabicyclo[3.2.0]heptane-2-carboxylic acid diphenylmethyl ester 4,4-dioxide and 4 mL of dry N,N-dimethylformamide. The resultant solution was cooled to −30° C. and a solution of 0.159 g 1,5-diazabicyclo[5.4.0]undec-5-ene in 3 mL N,N-dimethylformamide was added dropwise. The reaction was stirred for 3 hr at −30° C. and then processed in the same manner as the reaction mixture of Example 10. Crystallization of the product from ethyl acetate/ether/petroleum ether gave material identical to that obtained in Example 11, Method A.

EXAMPLE 12

[2S-(2α,4α,6α)]-4-Methyl-8-oxo-5-thia-1-azatricyclo[4.2.0.0$^{2,4}$]octane-2-carboxylic acid 5,5-dioxide Method A.

A 500 mL Parr bottle was charged with 0.958 g (2.4 mmol) of [2S-(2α,4α,6α)]-4-methyl-8-oxo-5-thia-1-azatricyclo[4.2.0.0$^{2,4}$]octane-2-carboxylic acid diphenylmethyl ester 5,5-dioxide, 100 mL of ethyl acetate and 1.0 g of 10% Pd/C. The mixture was shaken under 40 lbs. of hydrogen pressure for 1½ hrs, filtered to remove the catalyst and the filtrate extracted two times with 25 mL portions of 5% aqueous sodium bicarbonate. The aqueous phase was separated and adjusted to pH 2 with conc. hydrochloric acid. It was extracted two times with 50 mL portions of ethyl acetate. The extracts were combined, dried over sodium sulfate and concentrated to yield [2S-(2α,4α,6α)]-4-methyl-8-oxo-5-thia-1-azatricyclo[4.2.0.0$^{2,4}$]octane-2-carboxylic acid 5,5-dioxide as a white solid. Trituration with ether gave material which was identical to the sulfone carboxylic acid isolated in Example 4.

Method B.

A round-bottom flask equipped with argon bubbler was charged with 0.769 g (1.94 mmol) of sulfone starting material and 4.0 mL of anisole. The resultant solution was cooled to 0° and 20 mL of previously cooled trifluoroacetic acid was added. The reaction mixture was stirred at 0° for 1 hour, concentrated in vacuo and the residue partitioned between 50 mL of ethyl acetate.

The aqueous phase was extracted once with 50 mL of ethyl acetate and the organic phases were combined. The resultant ethyl acetate solution was washed two times with 25 mL portions of 5% aqueous sodium bicarbonate. The combined bicarbonate extracts were adjusted to pH 2 with 2 N hydrochloric acid and extracted with two 50 mL portions of ethyl acetate. The combined organic extracts were dried over anhydrous sodium sulfate, filtered and the filtrate concentrated in vacuo to yield a light yellow semi-solid. Subjecting the semi-solid to a repetition of the bicarbonate extraction sequence gave a solid which on crystallization from methanol/ether/petroleum ether gave a sulfone carboxylic acid as white crystals. This material was identical to the sulfone carboxylic acid isolated in Example 4.

EXAMPLE 13

[2S-(2α,3β,5α)]-3-Bromomethyl-3-methyl-7-oxo-4-thia-1-azabicyclo[3.2.0]heptane-2-carboxylic acid diphenylmethyl ester 4,4-dioxide Method A.

To a solution consisting of 4.62 g (10 mmol) of sulfoxide A (described in Example 9) and 50 mL of chloroform was added a solution consisting of 4.2 g m-chloroperbenzoic acid and 50 mL of chloroform. The reaction mixture was then heated at 55° C. for 1½ hr, allowed to cool, washed with saturated bicarbonate and with brine/water (1:1). The organic phase was dried over anhydrous sodium sulfate, filtered and concentrated to yield a yellow foam. Chromatography of the foam on silica gel (ethyl acetate/hexane; 1:2) yielded the title compound as a white foam.

Method B.

To a solution consisting of 2.1 g (4.5 mmol) of sulfoxide B (described in Example 9) and 15 mL of chloroform was added a solution consisting of 1.01 g m-chloroperbenzoic acid and 15 mL chloroform. The solution was stirred at ambient temperature for 15 hr and then subjected to a work-up similar to that used in Method A. Chromatography on silica gel (ethyl acetate/hexane; 1:2) yielded the title compound as a white foam.

What is claimed:

1. A compound of the formula

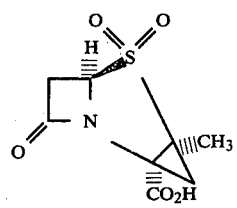

and the pharmaceutically acceptable salts thereof.

2. A compound of the formula

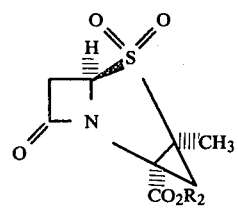

wherein R$_2$ is a conventional carboxy protecting group.

3. A compound of the formula

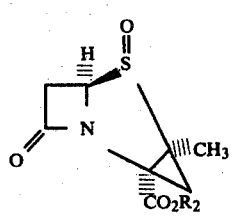

wherein $R_2$ is hydrogen or a conventional carboxy protecting group.

4. A compund of the formula

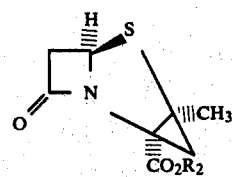

wherein $R_2$ is hydrogen or a converted carboxy protecting group.

5. A compound of the formula

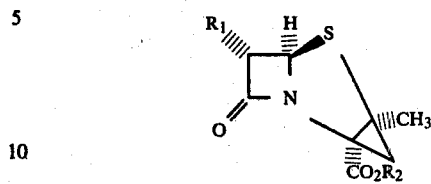

wherein $R_1$ is chloro, bromo or iodo and $R_2$ is hydrogen or a conventional carboxy protecting group.

6. A compound of the formula

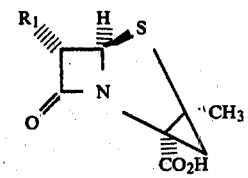

wherein $R_1$ is chloro, bromo or iodo.

* * * * *